United States Patent
Regn

[19]

[11] Patent Number: 6,041,249
[45] Date of Patent: Mar. 21, 2000

[54] DEVICE FOR MAKING A GUIDE PATH FOR AN INSTRUMENT ON A PATIENT

[75] Inventor: Judith Regn, Nuremburg, Germany

[73] Assignee: Siemens Aktiengesellschaft, Munich, Germany

[21] Appl. No.: 09/034,565

[22] Filed: Mar. 4, 1998

[30] Foreign Application Priority Data

Mar. 13, 1997 [DE] Germany ............................. 197 10 493
Jan. 16, 1998 [DE] Germany ............................. 198 01 446

[51] Int. Cl.⁷ ..................................................... A61B 6/00
[52] U.S. Cl. ............................ 600/429; 606/130; 378/20; 378/206
[58] Field of Search ..................................... 600/429, 407; 378/205, 206, 20; 606/130; 356/399

[56] References Cited

U.S. PATENT DOCUMENTS

| | | |
|---|---|---|
| 4,117,337 | 9/1978 | Staats . |
| 4,242,587 | 12/1980 | Lescrenier . |
| 4,293,771 | 10/1981 | Lescrenier . |
| 5,206,893 | 4/1993 | Hara . |
| 5,598,269 | 1/1997 | Kitaevich et al. . |
| 5,657,368 | 8/1997 | Rockseisen . |
| 5,782,842 | 7/1998 | Kloess et al. . |

FOREIGN PATENT DOCUMENTS

| | | |
|---|---|---|
| 44 12 164 | 10/1995 | Germany . |
| 195 01 069 | 7/1996 | Germany . |

*Primary Examiner*—Marvin M. Lateef
*Assistant Examiner*—Shawna J Shaw
*Attorney, Agent, or Firm*—Hill & Simpson

[57] ABSTRACT

A computed tomography apparatus is equipped with a device for marking a guide path on a patient for a medical instrument to be used in a medical procedure, such as a puncturing needle. The computed tomography apparatus produces a planning image, and a guide path is identified within the planning image. A computer, using the planning image and the path identified thereon, automatically adjusts a position of a light source, and if necessary a patient table on which a patient is supported, so that a beam from the light source is positioned to coincide with the guide path identified on the image.

4 Claims, 2 Drawing Sheets

DEVICE FOR MAKING A GUIDE PATH FOR AN INSTRUMENT ON A PATIENT

BACKGROUND OF THE INVENTION

1. Field of the Invention

The present invention relates to a device for making the guide-path for an instrument on a patient, particularly for a puncturing needle used in a medical procedure.

2. Description of the Prior Art

The puncturing of different body parts and organs for diagnostic or therapeutic purposes is known. In this way, tissue samples for examination can be obtained. It is often problematic to direct the puncturing needle safely to the desired location, especially when dealing with a relatively small area lying deep under the skin surface.

In preparation for puncturing, it is known to create sectional images of the body area to be punctured with the aid of tomography apparatus, e.g. a computed tomography or a magnetic resonance tomography apparatus. Using these sectional images, the physician determines the area to be punctured and selects the most favorable point and direction of incision. The patient is moved out of the tomography apparatus for puncturing. The point of incision found using the selected sectional image is marked on the patient's body. The physician subsequently inserts the puncturing needle, estimating the angle of incision.

An apparatus for assisting in such procedures is known from German OS 195 01 069, wherein two planar laser beams of different colors are directed onto the patient's body for more exact guidance of a puncturing needle. The line of intersection of the laser beams marks therein the guide path for the puncturing needle. The outlay for such a marking device is relatively significant.

SUMMARY OF THE INVENTION

It is an object of the present invention to provide a simplified marking device for guiding a puncturing needle in a medical procedure.

The above object is achieved in accordance with the principles of the present invention in a device for marking a guide path on a patient of an instrument used in a medical procedure, having a light source which emits a light beam, the light source being translatable and rotatable relative to a guide rail, and wherein a computer is provided with a planning image, such as tomography, e.g. a computed tomography slice image, and the light source is positioned by the computer dependent on the planning image. The computer can also position a patient table on which the patient is supported. The planning image is shown on a display, and points and angles are marked on the screen of the display so that the light source is positioned to direct the light beam in a path corresponding to the path to be followed by the medical instrument.

In the inventive device, the determination of a path for a puncturing needle ensues in a tomogram which prescribes the point of incision and the target point. This path is subsequently described by the coordinates of the point of incision, the angle of incision and the depth of incision. The point of incision and the angle of incision are indicated by a light beam, preferably a laser beam, and the table with the patient is automatically positioned for marking and for incision. The incision then ensues in the direction of the light beam in accordance with the prescribed depth of incision.

DESCRIPTION OF THE PREFERRED EMBODIMENTS

Figure 1:
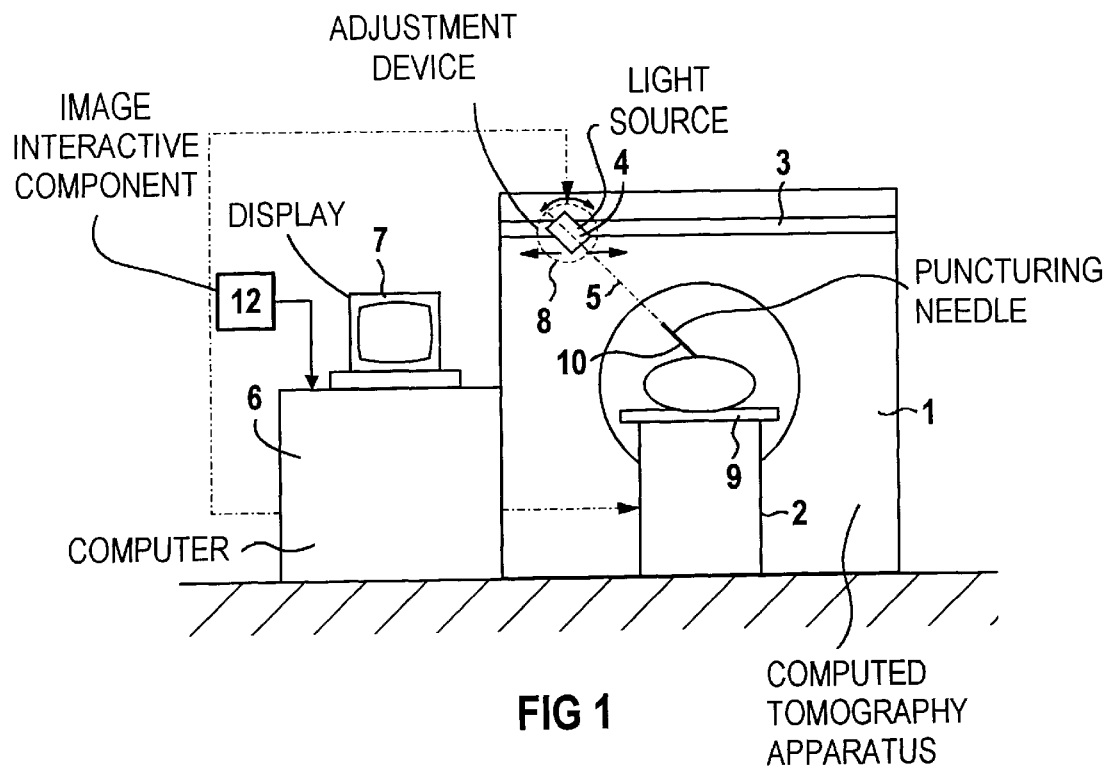
FIG. 1 is an end view of a computed tomography apparatus employing a marking device in accordance with the principles of the present invention.
Figure 2:
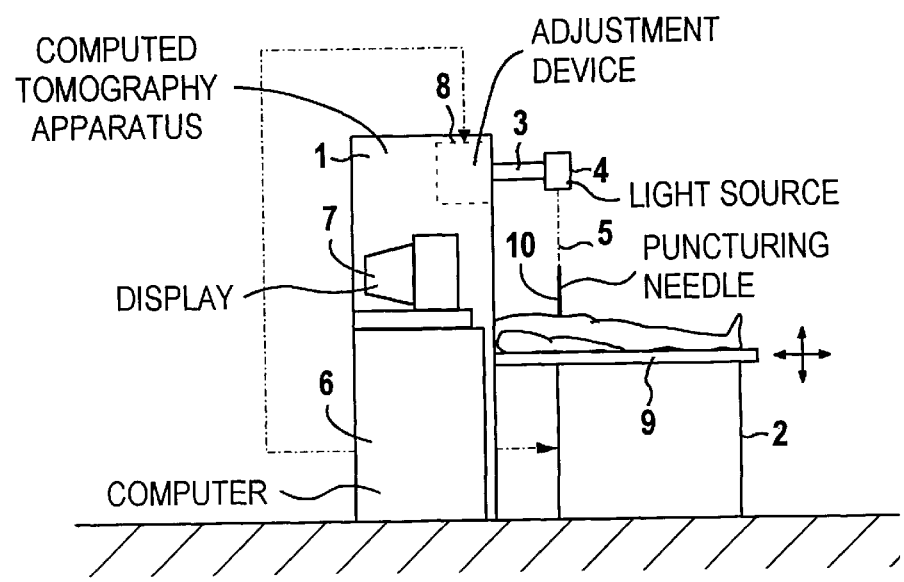
FIG. 2 is a side view of the computed tomography apparatus shown in FIG. 1.

FIGS. 1 and 2 show a computed tomography apparatus 1 having a pedestal (base) 2 on which a table 9 is mounted so as to be positionable by the pedestal thereto in directions in the plane of the table 9 as well as in height, as indicated by the arrows in FIG. 2. A patient lies on the table 9. The computed tomography apparatus 1 includes a rail 3 for guiding a light system 4, especially a laser radiation source, this light system emitting a guiding light beam 5.

Figure 3:
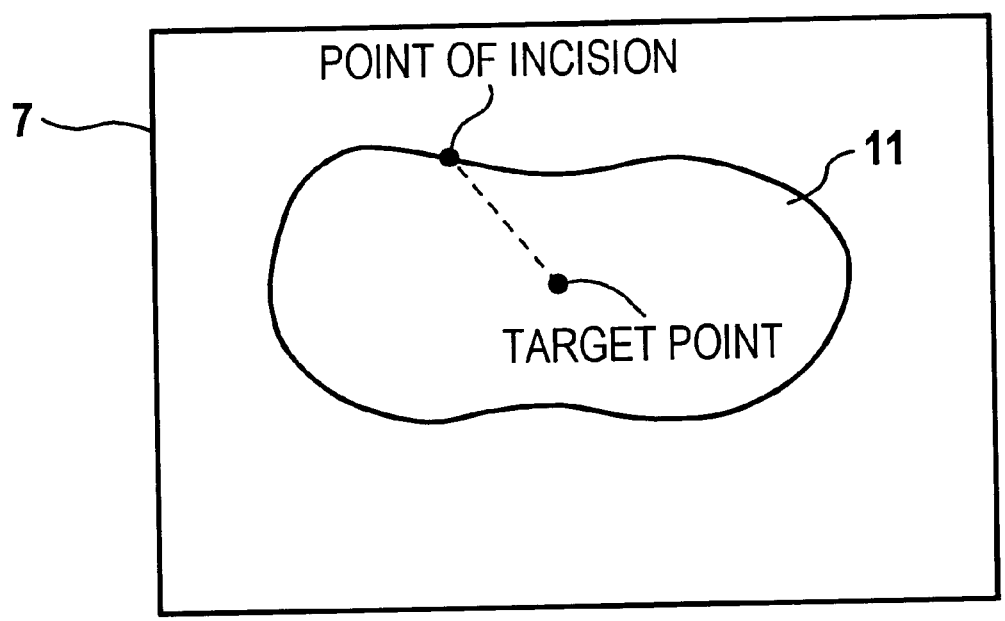
FIG. 3 schematically illustrates a planning image produced and used in accordance with the invention.

As shown in FIG. 3, point of incision and the target point are prescribed in a planning image 1 (tomogram) obtained using the apparatus 1. The angles between the straight line running through the two points and the perpendiculars thereto are determined subsequently. The light system 4, mounted on the rail 3 in a displaceable fashion, is automatically positioned (rotated and translated) using the planning image and if necessary the table 2 is also positioned until the light beam 5 shows on the patient's surface in the slice plane of the planning image. For insertion, an interventional instrument such as puncturing needle 10 is placed on the point of incision and the angle is adjusted until the light beam 5 is discernible on the top end of the needle 10. The needle 10 is subsequently inserted by the distance (i.e., to the depth) measured in the planning image. The physician must ensure that the light beam 5 is always discernible on the top surface of the needle. Lastly, the position of the needle 10 is checked through another CT-image.

A computer 6 calculates an image 11 of a slice of the patient's examined body area from the output signals of the x-ray source/radiation detector system of the computed tomography apparatus 1. This image 11, as shown in FIG 3, is reproduced on a monitor 7. It serves as a planning image for the prescribing the point of insertion and the target point for the puncturing needle 10. The angles between the straight line running between the two points and the perpendiculars thereto are also determined on the basis of the planning image by marking thereon with a suitable image-interactive component 12 such as a mouse or a light pen a touch pad or screen or a keyboard-controlled cursor. The computer 6 then effects an automatic adjustment of the light system 4 via an adjustment device 8 as well as adjusting the table 9 so that the patient and the light beam are correctly relatively oriented for the insertion of the needle 10 described above.

Although modifications and changes may be suggested by those skilled in the art, it is the intention of the inventor to embody within the patent warranted hereon all changes and modifications as reasonably and properly come within the scope of his contribution to the art.

I claim as my invention:

1. A device for use with a tomography apparatus, said device marking a guide path on a patient for an instrument, said device comprising:

means for producing a planning image of a slice of a patient;

a single light source which emits only a single laser line beam;

means for mounting said light source and for positioning said light source relative to the patient;

a table on which the patient is supported; and means for defining, in said planning image, a guide path proceeding intracorporeally into the patient for an interventional instrument and means for automatically displacing at least ne of said light source, via said means for mounting, and said table for positioning said laser line beam relative to said patient so that said laser line beam is co-linear with the guide path defined in said planning image so that said laser line beam forms a visual guide for conducting an interventional procedure.

2. A device as claimed in claim 1 wherein said light source comprises a laser.

3. A device as claimed in claim 1 wherein said means for mounting said light source comprises a guide rail and a mount to which said light source is attached, said mount being rotatable relative to said guide rail and slidable along said guide rail.

4. An interventional surgical apparatus comprising:

a tomography apparatus including means for producing a planning image of a slice of a patient;

a single light source which emits only a single coherent laser line beam; means for mounting said light source and for positioning said light source relative to the patient;

a table on which the patient is supported;

an interventional surgical instrument; and means for defining, in said planning image, a guide path proceeding intracorporeally into the patient for said interventional instrument and means for automatically displacing at least one of said light source, via said means for mounting, and said table for positioning said laser line light beam relative to said patient so that said laser line light beam is co-linear with the guide path defined in said planning image, so that said laser line beam forms a visual guide for conducting an interventional procedure with said interventional instrument.

* * * * *

UNITED STATES PATENT AND TRADEMARK OFFICE
CERTIFICATE OF CORRECTION

PATENT NO. : 6,041,249
DATED : March 21, 2000
INVENTOR(S) : Judith Regn

It is certified that error appears in the above-identified patent and that said Letters Patent is hereby corrected as shown below:

On the title page, item [54] and column 1:

In the title, cancel "MAKING" and substitute --MARKING-- therefor.

Signed and Sealed this

Sixth Day of March, 2001

Attest:

NICHOLAS P. GODICI

Attesting Officer   Acting Director of the United States Patent and Trademark Office